United States Patent [19]

Price et al.

[11] Patent Number: 5,192,683
[45] Date of Patent: Mar. 9, 1993

[54] MONOCLONAL ANTIBODIES TO CRUCIFORM DNA STRUCTURE

[75] Inventors: Gerald Price, Montreal; Maria Zannis-Hadjopoulos, Westmount, both of Canada; Lori Frappier, New York, N.Y.

[73] Assignee: The Royal Institution for the Advancement of Learning (McGill University), Quebec, Canada

[21] Appl. No.: 223,610

[22] Filed: Jul. 25, 1988

Related U.S. Application Data

[63] Continuation-in-part of Ser. No. 16,356, Feb. 19, 1987, abandoned.

[51] Int. Cl.$^5$ .................. C12N 5/20; C12N 15/02; C07K 15/28; C12P 21/08
[52] U.S. Cl. ..................... 435/240.27; 530/388.21; 435/70.21; 435/172.2
[58] Field of Search ............... 530/387, 388, 395, 806, 530/808, 828; 424/85.8; 435/6, 7, 70.21, 172.2, 240.26; 436/542, 548

[56] References Cited

U.S. PATENT DOCUMENTS

| | | | |
|---|---|---|---|
| 4,721,669 | 1/1988 | Barton | 435/6 |
| 4,792,520 | 12/1988 | Starnbrook et al. | 435/6 |
| 4,868,105 | 9/1989 | Urdea et al. | 435/6 |

OTHER PUBLICATIONS

Frappier et al., Characterization of the Binding Specificity of Two Anticruciform DNA Monoclonal Antibodies, The Journal of Biological Chemistry, vol. 264, No. 1, Jan. 5, 1989, pp. 334–341.

Frappier et al., Monoclonal Antibodies to Cruciform DNA Structures, Journal of Molecular Biology, vol. 193, No. 4, Feb. 20, 1987, pp. 751–758.

Nordheim et al., Negatively Supercoiled Plasmids Contain Left-Handed 2-DNA Segments as Detected by Specific Antibody Binding, Cell, vol. 31, 309–318, Dec. 1982 (Part 1).

Tenen et al., J. Virology SG(1):293–297, 1985.
Nobile et al., Intervirology 25:158–171 1986.
Eilat et al., J. Immunology Kipps et al., Handbook of Expt'l. Immunol. vol. 4, Weir Ed., Blackwell Sci. Publ. 1986.

Primary Examiner—David L. Lacey
Assistant Examiner—Paula Hutzell
Attorney, Agent, or Firm—Cushman, Darby & Cushman

[57] ABSTRACT

The present invention relates to monoclonal antibodies of class IgG1 and IgM possessing among others the property to bind to stable heteroduplex cruciform DNA structures constructed from two DNA plasmids, to the hybrid cell lines producing such antibodies, to a method for producing the cell lines and to a method for enhancing DNA replication in a cell system containing cruciforms functioning as signals for the initiation of DNA replication.

12 Claims, 5 Drawing Sheets

```
                                                                    TGATG
                                                        GACCCATA....
                                                                    ...AC
                                                        GTGGGTAT
                                            A-T
                                            A T
                                            G C
                                            C G
                                            C G
                                            C G
                                            A T
                                            G C
                            AGCTT....AGCTGGTC              GACCCATA....TGATG
                            AA....TCGACCAG——CTGGGTAT....AC 21
                            67           pRGM 29 x pRGM 67

Fig. 1c
```

```
                                        CATA....TGCATG
                                        GTAT....AC
                            G
                            C G
                            C G
                            G C
                            A T
                            C G
                            G C
                            C G
                            A T
                            C G
                AGCTT....AGCT              CATA....TGCATG
                AA....TCGA                 GTAT....AC
                                    C G
                                    C G
                                    A T
                                    G-C 21
                29           pRGM 21 x pRGM 67

Fig. 1B
```

```
                                CATA....TGCATG
                                GTAT....AC
                    G
                    C G
                    G C
                    G C
                    A T
                    C G
                    G C
                    C G
                    C G
                    A T
                    C G
        AGCTT....AGCT              CATA....TGCATG
        AA....TCGA                 GTAT....AC
                    C G
                    C G
                    A T
                    G C
                    C G
                    G C
                    G C
                    G C
                    T A
                    T-A 21
        29       pRGM 21 x pRGM 29

MONOCLONAL ANTIBODIES TO CRUCIFORM DNA STRUCTURE

The present application is a continuation-in-part of application Ser. No. 016,356, filed Feb. 19, 1987 now abandoned.

BACKGROUND OF THE INVENTION

The presence of inverted repeat (palindromic) sequences in DNA is ubiquitous. Whether at the DNA or RNA level, their importance has been established for termination of transcription and for attenuation in prokaryotes (Rosenberg and Court in (1979) Annu. Rev. Genet. 13, 319-353). In addition, inverted repeats have been found at the origin of replication of many mammalian viruses including SV40, polyoma, BK and herpes simplex I viruses, as well as at the replication origin of several prokaryotes. It has recently been shown by Zannis-Hadjopoulos et al. (1984) J. Mol. Biol. 179, 577-586 that such sequences may also be important in the initiation of mammalian DNA replication, since it has been found that origin-rich monkey DNA segments are enriched for inverted repeats.

Inverted repeat sequences have the potential of forming cruciform symmetrical (stem-loop or hairpin) structures through intrastrand nucleotide pairing. Although the existence of cruciforms in vivo has not been directly demonstrated, their existence in vitro has. It has long been postulated that cruciforms may form transiently as regulatory signals, e.g. to act as the attachment site within DNA replication origins for proteins involved in replication (Hand, R. (1978) Cell 15, 317-325, and Mizuuchi et al. (1982) J. Mol. Biol. 156, 229-243). In support of this, Collins et al., (1982) Biochem. 21, 2414-3419 found that, while there were no S1 nuclease-sensitive sites in nonproliferating cells, the number of S1 sites increased when cells moved from Go to G1 and peaked at the onset of S phase. Lilley ((1980) Proc. Nat. Acad. Sci. U.S.A. 77, 6468-6472) and Panayotatos et al. ((1981) Nature 289, 466-470) have demonstrated that cruciform structures were sensitive to single-stranded specific nucleases like S1 by virtue of their single-strandedness at the tip of the hairpin.

Although double-stranded DNA is poorly immunogenic, monoclonal antibodies have been raised against such alternative DNA structures as Z-DNA and carcinogen-modified DNA.

Consequently, the usefulness of these antibodies for studying alternative DNA structures suggested that the preparation of a monoclonal antibody for the detection of cruciform DNA structures would be highly desirable.

As mentioned before, it has long been postulated that cruciforms may form transiently in vivo, to act as special regulatory signals on the DNA, for the initiation of DNA replication and serve as the attachment sites for the initiator proteins.

The ability to form a stem-loop (cruciform structure) is known to be essential for function of the origin of replication on the plasmid ColE1, for example, where mutations that disrupt folding result in replication failure. In this case, a multiple stem-loop structure is necessary for the association of a primer-precursor RNA with the DNA template prior to generation of the primer by RNase H cleavage; control of the confirmation of the primer precursor controls plasmid replication. The ability to assume this configuration is conserved among different ColE1 type origins despite considerable divergence in their primary structure. The potential for secondary structural interactions is also a characteristic of the regions surrounding the light (L) and heavy (H) strand replication origins ($O_L$ and $O_H$) of mitochondrial DNA.

In the case of L strand initiation of DNA synthesis, the stem-loop structure found at the origin is essential for initiation in vitro in a human mitochondrial system.

Although the cruciform conformation is energetically unfavoured in a relaxed DNA molecule, negative supercoiling favors it; studies using single strand specific nucleases and electron microscopy have provided evidence for the existence of cruciforms in a supercoil DNA. Furthermore, it was recently reported that a dominant factor in the kinetics of cruciform extrusion is the DNA sequence that flanks the inverted repeat, with the sequence of the inverted repeat itself having little or no influence. The flanking sequence with the dominant influence on cruciform kinetics is very AT-rich, acts in cis independent of polarity, and it can have an effect over distances of at least 100 bp.

Despite the evidence provided by the nuclease S1 digestion experiments that argues in favor of the existence of cruciforms, their existence in vivo has not been directly demonstrated, although the presence of a native cruciform structure has recently been reported in E. Coli.

The obtention of anti-cruciform monoclonal antibodies that could enhance DNA replication in cell systems containing cruciforms acting as promoters in DNA replication would also be desirable.

SUMMARY OF THE INVENTION

In accordance with the present invention, there is provided a hybrid cell line producing a monoclonal antibody of class IgG1, which antibody binds to constructed stable cruciform and modified cruciform as well as heteroduplex T-shaped DNA structures but does not bind to double stranded and single stranded linear DNA nor does it bind to single stranded DNA containing a single stem-loop (or hairpin).

A hybrid cell line producing a monoclonal antibody of class IgM has also been prepared. This antibody possesses the same characteristics as the IgG1 antibody except for the fact that it does not bind to heteroduplex T-shaped DNA structures.

It is therefore an object of the present invention to provide monoclonal antibodies possessing the properties mentioned above as well as the property to enhance the duplication of DNA in vivo.

It is yet another object of the present invention to provide monoclonal antibodies possessing the property to isolate amplicons from DNA. Other applications for the antibodies of the present invention will be described in the following pages.

Furthermore, there is provided a process for constructing said hybrid cell lines producing said monoclonal antibodies, which comprises the steps of immunizing mice with stable heteroduplex cruciform DNA constructed from two DNA plasmids, removing the spleens from said mice and making a suspension of the spleen cells, fusing said spleen cells with mouse myeloma cells in the presence of a fusion promoter, diluting and culturing the fused cells in separate wells in a medium which will not support the unfused cells, evaluating the supernatant in each well containing a hybridoma for the presence of antibody by using antibody-binding radioimmunoassay techniques and selecting and cloning a hybridoma producing antibody which reacts with cruciform and modified cruciform DNA structures. The monoclonal antibody produced by this cell line is then recovered from the supernatant liquid.

It is to be noted that cruciform structures are energetically unfavoured and therefore rapidly revert to linear molecules. Because of this fact, it becomes necessary to design alternate immunogens in the form of stable heteroduplexes constructed from two DNA plasmids said heteroduplexes each possessing at least one cruciform structure.

Both the subject hybridomas and the antibodies produced thereby are identified herein by the following designations: 2D3 for the antibody of class IgG1 and 4B4 for the antibody of class IgM. The subject hybridomas were deposited on Feb. 18, 1987 at the American Type Culture Collection, 12301 Parklawn Drive, Rockville, Md. 20852, and were given the respective ATCC accession numbers HB 9328 and HB 9329.

Also within the scope of the present invention is a method for enhancing DNA replication in a cell system containing cruciforms functioning as signals for the initiation of DNA replication. This method comprises suspending cells containing cruciforms functioning as signals for the initiation of DNA replication in a media containing anti-cruciform monoclonal antibodies, permeabilizing the cells by adding to the suspension a permeabilizing buffer, and allowing DNA replication at a temperature ranging from 30° C. to 39° C. for a time ranging between 30 and 60 minutes.

The preparation and characterization of the hybridoma and the resultant antibody will be better understood by referring to the following description.

DETAILED DESCRIPTION OF THE INVENTION

The method of preparing the hybrid cell line of the present invention generally comprises the following steps:

A. immunizing mice with a stable heteroduplex cruciform DNA constructed from two DNA plasmids. While it has been found that female BALB/c mice are preferred, it is contemplated that other mouse strains could be used. The immunization schedule and heteroduplex cruciform DNA concentration should be such as to produce useful quantities of suitably primed splenocytes. Four immunizations at fourteen day intervals with 50 μg of a mixture of stable heteroduplex cruciform and homoduplex linear DNA mixed with an equal volume of 1% methylated bovine serum albumin has been found to be effective;

B. removing the spleens from the immunized mice and making a spleen suspension in an appropriate medium. These experimental techniques are well-known;

C. fusing the suspended spleen cells with mouse myeloma cells from a suitable cell line by the use of a suitable fusion promoter. Many mouse myeloma cell lines are known and available, generally from members of the academic community or various deposit banks. The cell line used should preferably be of the so-called "drug-resistant type, so that unfused myeloma cells will not survive in a selective medium, while hybrids will survive. The most common class is 8-azaguanine resistant cell lines, which lack the enzyme hypoxanthine guanine phosphoribosyl transferase and hence will not be supported by HAT (hypoxanthine, aminopterin and thymidine) medium. It is also generally preferred that the myeloma cell line used be of the so-called "non-secreting" type, in that it does not itself produce any antibody, although secreting types may be used. While the preferred promoter is polyethylene glycol having an average molecular weight from about 1000 to about 4000 (commercially available as PEG 1000, etc.) other fusion promoters known in the art may be employed;

D. diluting and culturing in separate containers, the mixture of infused spleen cells, unfused myeloma cells, and fused cells in a selective medium which will not support the unfused myeloma cells for a time sufficient to allow death of the unfused cells (about one week). The dilution may be a type of limiting one, in which the volume of diluent is statistically calculated to isolate a certain number of cells in each separate container (e.g. each well of a microtiter plate). The medium is one (e.g. HAT medium) which will not support the drug resistant (e.g. 8-azaguanine resistant) unfused myeloma cell line. Hence, these myeloma cells perish. Since the unfused spleen cells are non-malignant, they have only a finite number of generations. Thus, after a certain period of time (about one week) these unfused spleen cells fail to proliferate. The fused cells, on the other hand, continue to proliferate because they possess the malignant quality of the myeloma parent and the ability to survive in the selective medium;

E. evaluating the supernatant in each container (well) containing a hybridoma for the presence of antibody; and F. selecting (e.g. by limiting dilution) and cloning hybridomas producing the desired antibody.

The novel antibodies of the present invention may be used in diagnostic and research or investigation procedures as well as in commercial and biological applications.

As an example of diagnostic and research or investigation procedures there may be mentioned the following:
A. Detection and isolation of cruciforms with associated gene elements (e.g. amplicons or naturally occurring genes with proximity to replication signals as represented by DNA cruciforms).
B. Enumeration of replication signals in states of cell cycle, growth, and dysplasia.
C. Selection of a minority-represented plasmid by depletion of replicating-selected plasmid in a mixed population.
D. Alteration of transcription in vitro and gene expression in a selective system.
E. Alteration of transcription in vivo to detect cell cycle regulation cell, cycle-regulated genes, and genes regulated through cruciform-structural recognition signals.
F. Interference with and control of virus-eukaryotic cell recombination mechanisms.

As an example of commercial and biological procedures there may be mentioned the following:
A. Development of an in vitro defined acellular system for replication of gene elements.
B. Development of an in vitro defined acellular system for replication, transcription, and translation of isolated genes (i.e. in vitro gene to gene product system).
C. Potential use to control mutations and mutation rate in yeast through interference with recombination of the 2 micron plasmid of yeast with itself and the yeast chromosome.

The monoclonal antibodies of the present invention are specific to cruciform DNA. When it is desired to use these antibodies for enhancing DNA replication in cells containing cruciforms functioning as signals for the initiation of DNA replication, the following procedure may be employed.

In order that the monoclonal antibodies of the present invention may be used for enhancing DNA replication, it is necessary to employ cells containing cruciforms functioning as signals for the initiation of DNA replication. For example, the cells may be selected from CV-1, COS-7, WI 38HeLa and the like.

The targetted cells are suspended in a media containing the anti-cruciform monoclonal antibodies. The media containing the antibodies can be selected from alpha medium containing hypoxanthine, thymidine, insulin, transferrin, selenium and 2% FCS. The cell concentration may vary from $2 \times 10^5$ to $1 \times 10^6$ cells/ml while the concentration of the antibodies will usually range between 2 and 5 µg/ml.

Once the cells have been suspended in the antibody containing media, a permeabilizing buffer is added to the suspension. Various types of permeabilizing buffers such as Nonidet-P40 and Triton X-100 Hepes buffers may be contemplated for use in the method of the present invention.

Once the cells have been contacted with both the permeabilizing buffer and the anti-cruciform antibodies of the present invention, the native chromatin contained in the cells is immediately exposed to the antibodies. Following an incubation period that may range from 30 to 60 minutes at a temperature that may vary from 2° C. to 10° C., in order to allow binding to occur between the antibody and the cruciforms present on the chromatin, the DNA may be replicated for 30 to 60 minutes at a temperature that may vary from 30° C. to 39° C.

Using the technique described above, the monoclonal antibodies directed against cruciform DNA effectively enhance the incorporation of labeled precursor nucleotide into acid precipitable material by 2 to 6-fold, while the same effect is not observed in the presence of control antibodies.

The synthesis process and products of the present invention will be more readily illustrated by referring to the following examples which do not intend to limit the present invention thereto.

EXAMPLE 1

Construction of Stable Heteroduplex Cruciform and Non-Cruciform DNA Structures

Figure 1A:
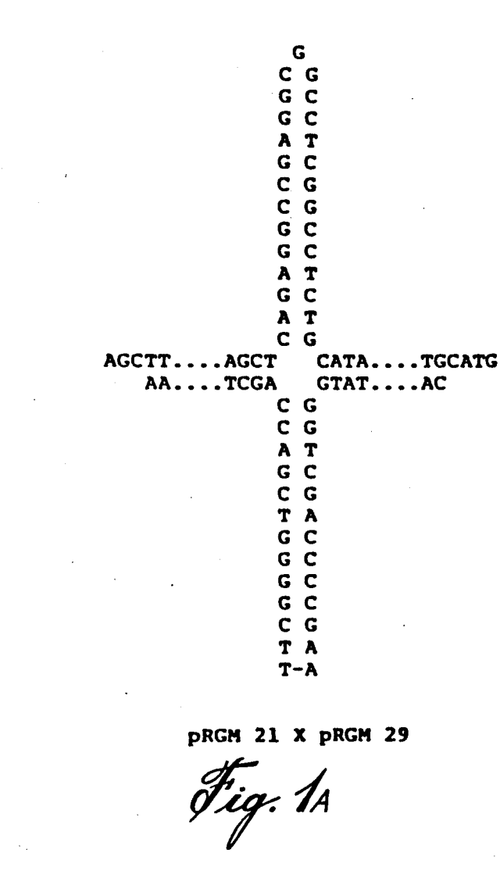
FIG. 1(A) represents the structure of a pRGM 21 × pRGM 29 heteroduplex.
Figure 1B:
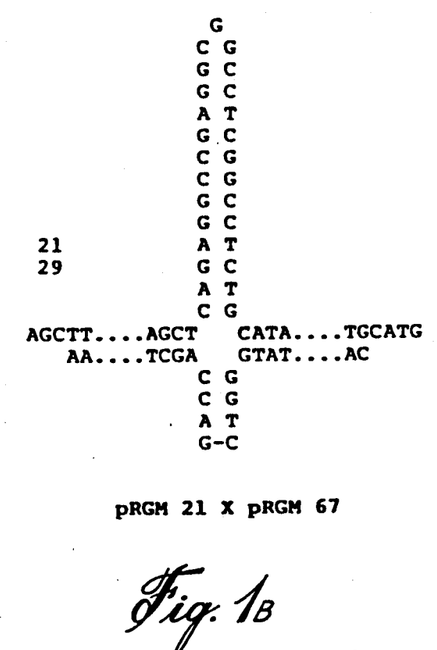
FIG. 1(B) represents the structure of a pRGM 21 × pRGM 67 heteroduplex.
Figure 1C:
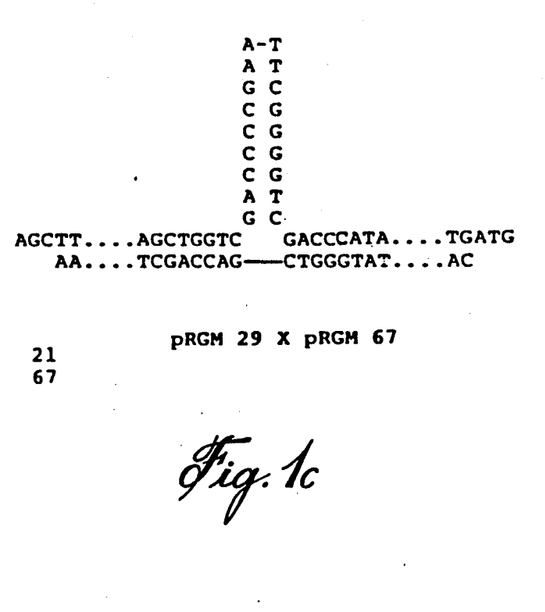
FIG. 1(C) represents the structure of a pRGM 29 × pRGM 67(C) heteroduplex.

The plasmids pRGM 21, pRGM 29 and pRGM 67 whose construction is described by Nobile and Martin in (1986) Intervirol. 25, 158-171 were used by Nobile and Martin for construction of the heteroduplexes represented in FIG. 1. pRGM 21 consists of the wild type SV40 origin of replication, from nucleotide 5172 clockwise through 5243/0 to 132 (200 bp; SV "BB" numbering system, used by Tooze in (1981) DNA tumor viruses, molecular biology of tumor viruses, 2nd ed., part 2 revised. Cold Spring Harbor Laboratory, Cold Spring Harbor, N.Y.), inserted between the HindIII and SphI sites of pBR322. In pRGM 29, the 27-bp comprising the 13 bp palindrome in pRGM 21 have been replaced by a 26-bp sequence, composed of 2 SalI and one EcoRI linkers, giving rise to a 13-bp palindrome that bears no sequence similarity to that of wild type SV40. In pRGM 67, the 13 bp inverted repeat of pRGM 21 is substituted with an 8-bp SalI linker containing a 4 bp palindrome. Single stranded wild type SV40 origins were isolated from mSV01 single-stranded circular DNA as described by Hay et al. in (1982) Cell 28, 767-779. MSV01 was digested with BamHI to generate two fragments and the small fragment, containing the wild type SV40 origin, was purified. This fragment contains a 13-bp stem-loop structure. To generate linear ss DNA, the stem-loop structure in this SV40 origin was cleaved by HaeIII.

To construct the heteroduplexes, pRGM 21 and pRGM 29 were digested with HindIII and SphI prior to heteroduplexing. The resulting fragments were concentrated by ethanol precipitation and then resuspended in 1 mM Tris-HCl (pH 7.5), 0.1 mM EDTA. The ds fragments were denatured at pH 11 by adding 1M NaOH, 3M NaCl, to a final concentration of 0.5M and 1.5M, respectively. After 5 minutes, the solution was neutralized by adding 250 mM Tris-HCl (pH 7.5), 25 mM EDTA (final concentration: 10 mM NaOH, 10 mM Tris, EDTA), and the DNA was incubated at 68° C. for 2 hours to allow reannealing to occur. The DNA was then precipitated in ethanol and stored in 10 mM Tris (pH 7.5), 1 mM EDTA at −20° C. This procedure yielded approximately equal amounts of homoduplex and heteroduplex molecules, as assessed by electrophoresis on acrylamide gels, which technique is described in Example III.

EXAMPLE II

Production of Monoclonal Antibodies

A. Immunizations and Screening of Mice

Female BALB/c mice (age 11 weeks) were given four intraperitoneal injections at two week intervals. Each injection consisted of 50 μg (100 μl) of a mixture of the heteroduplexes and homoduplexes (HindIII/SphI fragments of pRGM 21 and pRGM 29), mixed with an equal volume of 1% methylated bovine serum albumin (Sigma Chemical Co.), and emulsified by vortexing with an equal volume of complete Freund's adjuvant (Sigma Chemical Co.). Prior to each injection, blood samples were obtained from the mice by tail bleeding. Serum was isolated from the blood as detailed by Groopman et al. in (1982) Cancer Res. 42, 3120–3124 and was diluted 1:10 and 1:20 for use in characterization of the respective activities of 2D3 and 4B4. While the 1:10 dilution of serum from immunized mice bound to both the hetero and the homoduplex DNA molecules, as indicated by the retardation of both bands, assays of the 1:20 dilution indicated more selective binding to the heteroduplex molecules. The selective binding observed with serum from immunized mice was considerably greater than that of the preimmune serum.

B. Cell Fusions and Cloning

Four days after the last injection, the spleen was removed and dissociated into a single cell suspension. The spleen cells were then fused with a mouse myeloma line, P3-X63Ag8, as previously described by O'Hara et al. in 1982 Immunol. letters 5, 15–18, and then aliquoted into 96-well flat-bottomed culture plates (Micro-wells, Linbro Scientific, Hamden, CT) in HAT-selective medium (minimal essential medium alpha containing hypoxanthine, aminopterin, thymidine and 20% FCS). After 8 days, cultures were re-fed with HT medium (alpha medium containing hypoxanthine, thymidine and 20% FCS) and 2 days later, hybridomas were present in approximately 600 microtiter wells. The day after, the fastest growing cells from 232 wells were transferred from the microwells to 24-well culture plates (Linbro Scientific, Hamden, CT). Seven days later, 20 μl of the supernatant culture fluid from each of the 232 wells containing fast growing cells was assayed for cruciform binding by radioimmunoassay. This technique will be further described in Example III. The radioimmunoassays indicated that 33 wells contained hybridomas producing antibodies to the cruciform-containing heteroduplex molecules while 12 other wells contained hybridomas producing antibodies that appeared to bind to both the homo- and heteroduplex molecules. The content of each of these 45 wells was then transferred in 25 cm² culture flasks, grown up to confluence in HT medium and re-tested for cruciform binding. Upon re-testing, several of the hybridomas were found to be unstable, leaving 10 hybridomas producing heteroduplex-specific antibody and one hybridoma producing antibody that seemed to bind to both homo- and heteroduplex molecules. Two of the heteroduplex-specific hybridomas, 2D3 and 4B4, were cloned by limiting dilution, and individual clones were screened for specific antibody production. In the limiting dilution method, three tubes of cells containing 50, 15 and 5 hybridoma cells per ml were prepared, and each of these was plated out into a 96-well culture plate at 0.2 ml per well. When macroscopic colonies appeared, supernatants from wells containing single colonies were assayed, and for each of the 2 hybridomas cloned, three positive clones from 4B4 and four from 2D3 were selected for further study.

C. Hybridoma Growth in Low Serum Medium

Clones 2D3 and 4B4 can be grown in low serum culture using the ITS cell growth system (Collaborative Research, Waltham, MA). Cell density saturated cultures of hybridomas growing in HT medium containing 20% FCS were harvested and the cells were resuspended in twice the volume of Dulbecco's Modified Eagles Medium containig insulin, transferin, selenium and 2% FCS. The cells were grown to saturation in the low serum medium (4 to 5 days), and then 2D3 and 4B4 culture supernatants were then tested for binding to the cruciform (FIG. 1A), to the modified cruciform (FIG. 1B), to the T-shaped molecule (FIG. 1C), to the single-stranded wt SV40 origin containing the 13-bp hairpin structure and to linear ss DNA. An excess of unlabeled form I SV40 DNA was included in each of these assays in order to counteract any non-specific binding of the antibodies to the various end-labeled DNAs. These results indicated strong binding of both 2D3 and 4B4 low-serum culture fluids to the cruciform and modified cruciform, weak (2D3) to negligible (4B4) binding to the T-shaped molecule and no binding at all to any of the linear homoduplex DNA components. Neither antibody bound to the ss linear or the stem-loop-containing ss SV40 origin DNAs, except for limited non-specific binding of 2D3 to the latter which was reduced by the addition of excess SV40 form I DNA. Identical results i.e. no bindings were also obtained upon testing the binding of 2D3 to two modified T-shaped molecules, pRGM 20×pRGM 21 and pRGM 20×pRGM 29 (1) and of 2D3 and 4B4 to the native form of yeast tRNA. Culture supernatants from these clones also did not bind to a 210-bp (RsaI to BamH1) linear pBR322 fragment with 16% homology to the SV40 origin. These findings are consistent with the idea that these two antibodies recognize determinants that are specific to the cruciform conformation of the nucleic acid.

D. Antibody Isotyping

An ELISA based isotyping kit for mouse immunoglobulin (Mouse Typer Sub-Isotyping Kit, Bio-Rad, Richmond, CA) was used to determine the isotype of the antibody in 2D3 and 4B4 serum-free culture fluid. The 2D3 monoclonal antibody was found to be $IgG_1$ and the 4B4 antibody IgM.

EXAMPLE III

Characterization of 2D3 and 4B4 Reactivities

The binding specificity of antibodies in the serum of immunized mice and of monoclonal antibodies was determined by a radioimmunoassay. For this assay, the HindIII/SphI digestion products of pRGM 21, 29 and 67 were separated electrophoretically on 4% acrylamide gels. The 200, 199 and 181 bp fragments, respectively, were eluted from the gel, extracted once with phenol and ether, and precipitated in 75% ethanol. For the screening of serum and hybridoma culture supernatants, the 200 and 199 bp fragments were used to make heteroduplexes, as described above, and for further studies of monoclonal antibody binding specificity the 181 bp fragment was used to construct heteroduplexes with each of the 200 and 199 bp fragments. The resulting mixture of homo- and heteroduplex molecules was then end-labeled at the 5'-ends with gamma-$^{32}$P-ATP using the method of Maxam and Gilbert described in (1980) Meth. Enzymol. 65 499-525, and was used for binding with the antibodies. For assays involving tRNA, ss DNA with a hairpin and ss linear DNA, these molecules were similarly end-labeled at their 5'-ends. Mouse serum to be assayed was diluted 1:20 with borate buffer (160 mM NaCl, 2 mM borate, pH 8), in a total volume of 20 µl. For assays of monoclonal antibodies, 2.2 µl of 10X borate buffer was added to 20 µl of hybridoma supernatant culture fluids. Approximately 60,000 cpm (1-2 nanograms) of the end-labeled molecules were added to each sample in borate buffer, and the mixture was incubated at 37° C. for 1 hour followed by 30 min on ice. Incubation mixtures also included excess (40-200 ng) supercoiled SV40 (form 1) DNA. The assay mixture was then electrophoresed on a 5% polyacrylamide gel, and the gel was dried and autoradiographed using the method described in (1984) Cell 37, 889-901. Appropriate negative controls for cruciform binding were included in each assay and 5 µl of an SV40 T antigen crude extract preparation, which binds to SV40 origin sequences in both the homoduplex and heteroduplex DNAs, was used as a positive control.

The applicability of the "band competition" assay, used by Strauss and Varshavsky ((1984) Cell 37, 889-901) for detecting DNA binding proteins in crude extracts, was also tested successfully for detecting antibody with binding specificity to cruciform DNA. These positive results confirm the findings of Tenen et al. in (1985) J. Virol. 56, 293-297, where the ability of T antigen to bind to both linear and cruciform SV40 DNA was shown by footprinting analyses.

Both the 2D3 and 4B4 monoclonal antibodies bound to the pRGM 21×pRGM 29 cruciform (FIG. 1A), and the pRGM 21×pRGM 67 modified cruciform (FIG. 1B) but only 2D3 bound to the pRGM 29×pRGM 67 T-shaped molecule (FIG. 1C) and neither 2D3 or 4B4 bound to any of the pRGM 21, 29 or 67 linear homoduplex molecules, to ss DNA nor to native yeast tRNA. This indicates that the binding specificity of these antibodies is directed at conformational determinants specific to cruciform structures that are present in both of these heteroduplex molecules, rather than at a specific DNA sequence. It is conceivable that 2D3 and 4B4 recognize either the tip (loop) of the stem-loop structure, where single-stranded regions are present, or the junction at the base of the stem, since in these areas the normal double helical conformation of linear ds DNA is disrupted because of conformational constraints introduced by the presence of the stem-loops or hairpins.

Since binding to the T-shaped structures (FIG. 1C) and the single-stranded SV40 origin was weak (2D3) or negligible (4B4) and since both of these molecules contain a stem-loop structure with an identical tip to the stem-loop structure of the cruciform (FIG. 1A) that is bound by 2D3 and 4B4, it is most likely that these antibodies recognize conformational determinants at the junction at the base of the stem. The weak binding to the T-shaped structure and to the ss SV40 origin by 2D3 was consistent in several separate experiments, and this binding was reduced when an excess of form I SV40 genomic DNA was included in the reaction mixture. Since binding to the cruciform and modified cruciform structures was unchanged by the addition of SV40 DNA, it is believed that the weak binding to the T-shaped structure and single-stranded SV40 origin represents non-specific antibody-DNA interactions. Antibodies to B-helical ds DNA, poly (dG-dC) Z-DNA, aflatoxin B1-modified DNA and tRNA all have been shown to recognize specific conformational determinants of their respective antigens. Anti-tRNA antibodies that are spontaneously produced in NZB/NZW mice do not recognize tRNA molecules whose conformation has been altered by formaldehyde treatment, and Eilat et al. ((1977) J. Immunol. 118, 1016-1024) have proposed that the single-stranded loops of the tRNA constitute the antigenic sites. Jacob and Tron ((1982) J. Immunol. 128, 895-898) found that anti-ds DNA antibodies from autoimmune mice did not recognize ss DNA or Z-DNA, and that the bases of ds DNA did not contribute to the antigenic site. They concluded that these antibodies were directed against the geometry of the pentose phosphate backbone and to some aspects of the double helical conformation of ds DNA. Similarly Nordheim et al. ((1982) Cell 31, 309-318) have suggested that antibodies against Z-DNA are not sequence specific but that these antibodies most likely recognize elements of the sugar phosphate backbone peculiar to the Z-DNA conformation. Presently, the possibility that 2D3 and 4B4 may have some specificity for particular nucleotides in addition to their conformational specificity cannot be ruled out.

2D3 and 4B4 antibodies may prove to be extremely valuable in the detection of cruciform structures which have been implicated in the initiation and termination of transcription as well as in the initiation of DNA replication.

EXAMPLE IV

Effect of 2D3 and 4B4 Monoclonal Antibodies on DNA Replication in Permeabilized Cells

A. Cells

CV-1 monkey cells were grown in Dulbecco's Modified Eagle's medium (DMEM) supplemented with 5% (v/v) fetal calf serum (FCS). The cells were then plated at $5 \times 10^5$ per 100 mm plate in the presence of 0.1 µCi/ml or 10 nCi/ml [$^3$H]thymidine (1 mCi/ml: 66 Ci/mmol: ICN) and were synchronised at the $G_1/S$ boundary by serum starvation and aphidicolin as described in Zannis-Hadjopoulos et al. (1984) J. Mol. Biol. 179, 577-586. Progression through S phase was monitored by removing the medium containing aphidicolin, washing the plates twice with phosphate buffered saline (PBS) and re-incubating the cultures in fresh media at 37° C. for up to 6 hours. Samples were taken at hourly intervals for analysis by flow cytometry as described in Kaufmann et al. (1985) Mol. Cell. Biol. 5, 721-727.

Figure 2A:
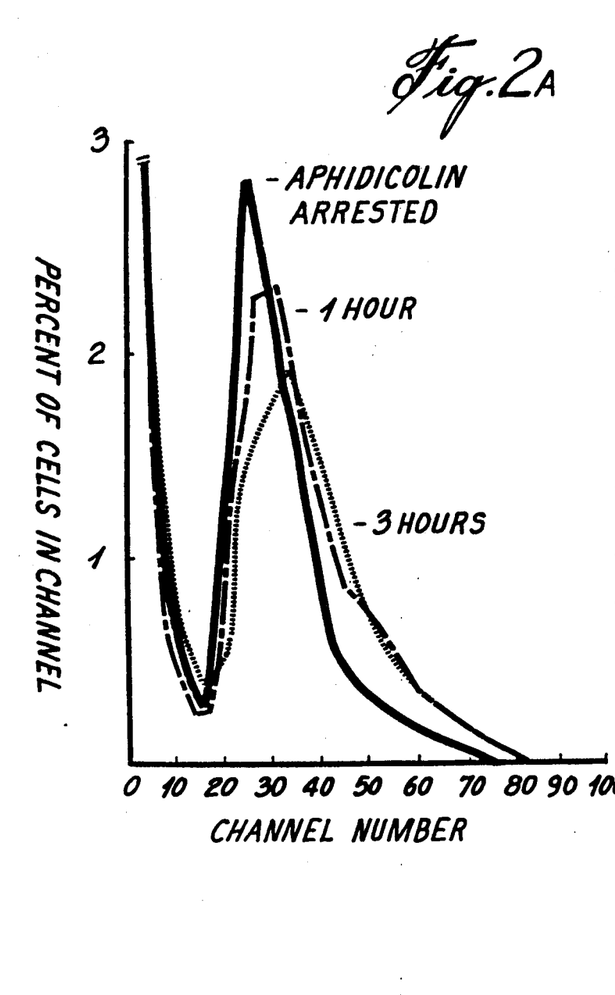
FIG. 2(A) represents the flow microfluorometric analysis of CV-1 cells blocked at $G_1/S$ with aphidicolin.
Figure 2B:
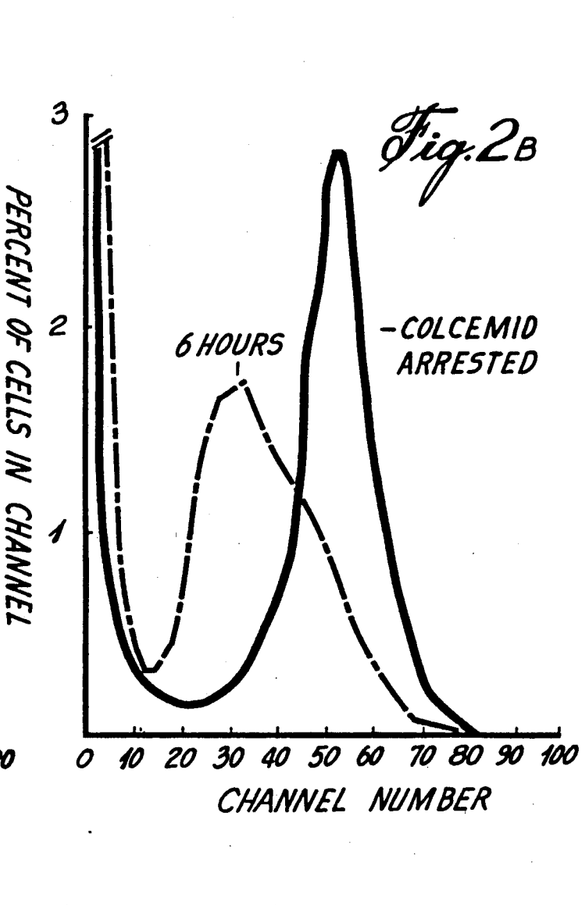
FIG. 2(B) represents the flow microfluorometric analysis of aphidicolin-treated CV-1 cells released into S phase.

The degree of synchrony achieved by this method was monitored by flow cytometry as shown in FIG. 2. The results show that after 16 hours in the presence of aphidicolin plus 20% serum, the vast majority of the viable cells were distributed in $G_1$ (FIG. 2A) but started synthesizing DNA within 1 hour after removal of the aphidicolin and continued for 3 hours. By 5 hours after removal of the drug the majority of the cells were still distributed in the early and mid-part of S phase with only a small fraction of cells in late $S/G_2$ phase (FIG. 2B).

B. Antibodies

The anti-cruciform antibodies to 2D3 and 4B4 described in Examples 1 to 3 were used as DNA replication enhancers. Monoclonal antibody P3 secreted by myeloma line P3-X63AG8 was used as control for the 2D3 antibody while the control for 4B4 was an unreactive IgM monoclonal antibody to rat myeloid cells BN18. An IgM monoclonal antibody to dsDNA (HB2;Biosoft), with reactivity to Z-DNA and B-DNA but not with ssDNA, poly dA-poly dT, poly d(AT), poly dT and RNA was used as an anti-DNA control antibody.

C. DNA Replication in Permeabilized Cells

The method described in Burhans et al (1986) Proc. Natl. Acad. Sci. U.S.A. 83, 7790-7794 was used. The synchronized cells were collected either at the $G_1/S$ interphase or at hourly intervals following the removal of aphidicolin by scraping the cells off the plates and centrifugation. The cell pellets were immediately put in ice and resuspended in 1 ml of ice-cold hybridoma culture supernatant containing the appropriate monoclonal antibody. The monoclonal antibody reactivities were all determined to be equivalent to the culture supernatants studied in Example III. The immunoglobulin concentration of both 2D3 and 4B4 is 5-10 μg/ml; HB2 was used in concentrations demonstrated to be equivalent to the DNA-binding activity of 2D3, as assessed by gel retardation assays described in Frappier et al., (1987) J. Mol. biol. 193, 751-758.

One volume of ice-cold 2X replication buffer [100 mM Hepes, pH 7.8, 200 μg heat inactivated, nuclease-free BSA; 2 mM DTT; 0.2 mM each dGTP, dTTP and dATP; 0.4 mM each CTP, GTP, UTP; 8 mM ATP: 30% glycerol; 20 mM MgCl$_2$; 2 μl [α-$^{32}$P]dCTP (3000 Ci/mmol; 10 mCi/ml; ICN)] containing 0.4% Nonidet P-40 (NP-40) and 2 mM phenylmethanesulfonylfluoride (PMSF) was immediately added to the cell-monoclonal antibody suspension (final monoclonal antibody dilution was 50%). In some experiments, aphidicolin (final concentration of 8 μg/ml) or 2',3'-dideoxythymidine triphosphate (ddTTP; final concentration of 50 μM) were included in the replication buffer. The mixture was incubated in ice for 30 minutes to allow the monoclonal antibody to enter the nucleus and bind to cruciform DNA; the mixture was then transferred to 37° C. for another 30 minutes to allow DNA replication to occur. The replication reaction was terminated either by the addition of 50% trichloroacetic acid (TCA) to a final concentration of 5%, followed by incubation in ice for 1 hour, collection of the acid precipitable material on GF/C filters, extensive washing with 5% TCA, drying and scintillation counting; or by the addition of an equal volume of 2× lysis buffer (2.4% SDS, 400 mM NaCl, 80 mM EDTA. 200 mM Tris-HCl, pH 7.9) and proteinase K to 200 μg/ml for subsequent extraction of high mol. wt DNA.

Figure 3A:
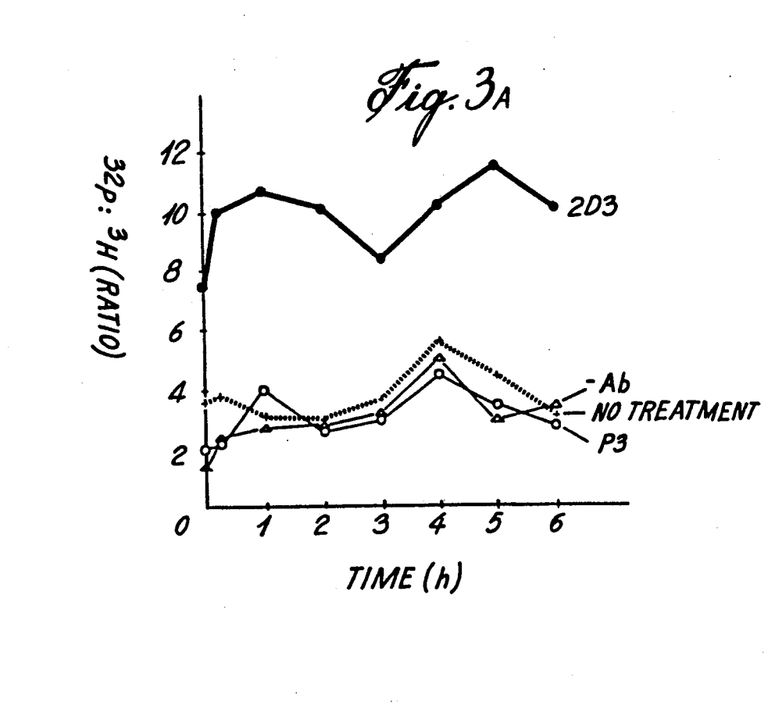
FIG. 3(A) represents the effect of anti-cruciform DNA monoclonal antibody 2D3 on the incorporation of $[\alpha\text{-}^{32}P]dCTP$ into acid precipitable material of permeabilized CV-1 cells.
Figure 3B:
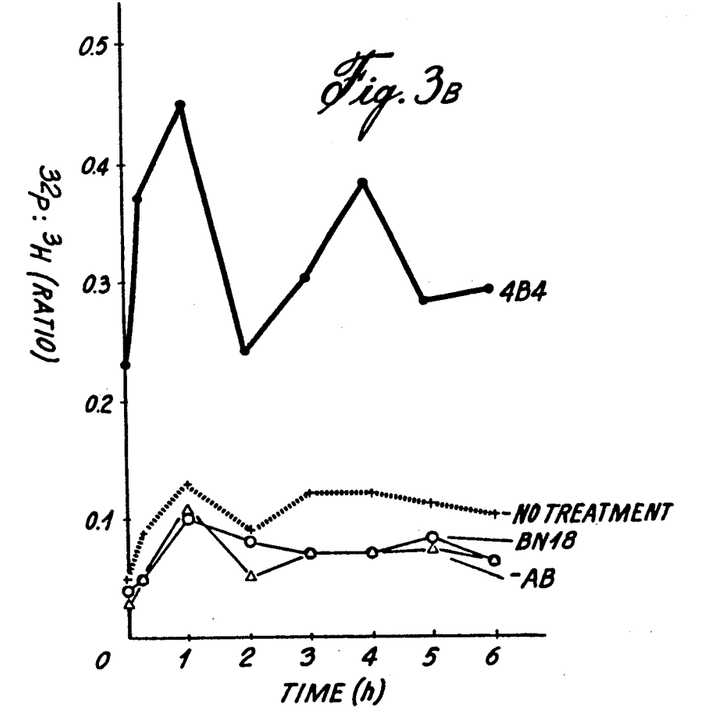
FIG. 3(B) represents the effect of anti-cruciform DNA monoclonal antibody 4B4 on the incorporation of $[\alpha\text{-}^{32}P]dCTP$ into acid precipitable material of permeabilized CV-1 cells.

The results, expressed as a $^{32}$P:$^3$H ratio to normalize for variation in cell numbers, show a 3- to 4-fold enhancement of [α-$^{32}$P]dCTP incorporation in the presence of 2D3 over that observed in the presence of P3 as demonstrated in FIG. 3A and a 4-5-fold enhancement in the presence of 4B4 over that observed in the presence of BN18 as shown in FIG. 3B. The incorporation profiles obtained in the presence of P3 and BN18 were identical to those obtained when the cells were resuspended in only ITS medium (-Ab) or PBS (no treatment).

Figure 4:
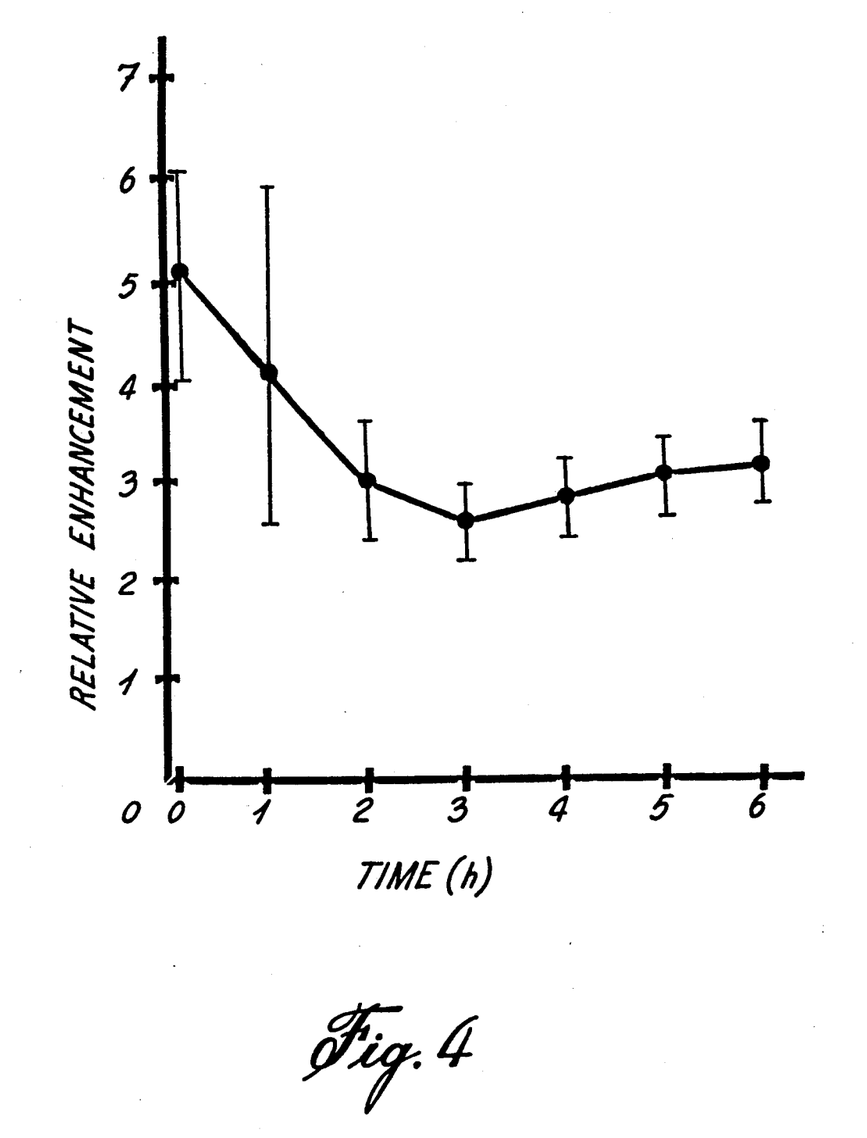
FIG. 4 represents relative enhancement of incorporation of radioactivity by the 2D3 antibody into acid precipitable material of permeabilized CV-1 cells.

FIG. 4 shows a plot of relative enhancement (stimulation of incorporation by 2D3 mAb over P3) at each time point, as an average of five different experiments (except for the 6 hours time point which is an average of three experiments). As the error bars indicate, although there is variability from experiment to experiment, especially during the first hour of synthesis, there is on the average a reproducible stimulation of synthesis by 2D3 at each time point, in excess of 3-fold.

Figure 5:
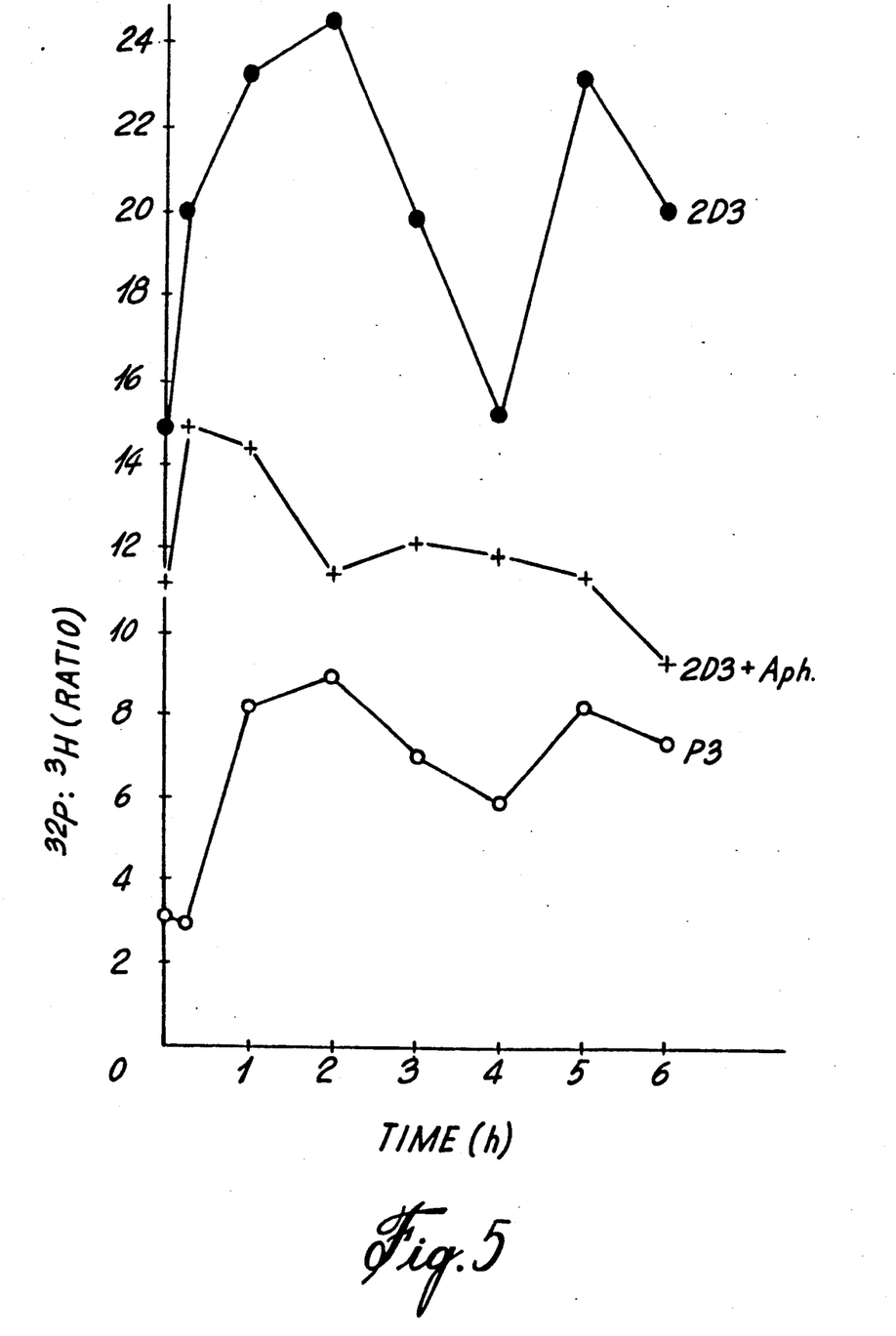
FIG. 5 represents the effect of aphidicolin on the enhancement by the 2D3 monoclonal antibody of incorporation of $[\alpha\text{-}^{32}P]dCTP$ into acid precipitable material of permeabilized CV-1 cells.

The majority of the enhanced incorporation (>50% at the 2 and 5 hours peaks in the case of 2D3) was sensitive to the action of aphidicolin at a concentration of 8 μg/ml as shown in FIG. 5, indicating that most of the synthesis observed was due to the action of DNA polymerase α and/or δ. The variation in relative aphidicolin effects may reflect the differences in the level of antibody-induced enhancement. In general, greater enhancement by 2D3 is associated with a greater sensitivity to aphidicolin. It can be noted that the majority of synthesis in permeabilized cells at the $G_1/S$ boundary was relatively insensitive to the action of aphidicolin (8 μg/ml), while at later time points in S, synthesis became increasingly sensitive to the drug. The reverse was true in the presence of 2',3'-dideoxythymidine triphosphate (ddTTP), a nucleotide analogue that inhibits polymerase β and γ but not α where maximal inhibition (50-60%) occurred within the first 15 minutes in S and decreased as cells progressed into S (data not shown). The incorporation of precursor nucleotide into DNA either in the presence of P3 control antibody or in the complete absence of any antibody (ITS medium or PBS) was also sensitive to this dose of aphidicolin (8 μg/ml), ranging from 22% inhibition at the $G_1/S$ boundary to 50% at the later time points.

In order to test further whether the observed enhancement of precursor incorporation into DNA was a specific effect of the anti-cruciform monoclonal antibodies, the effect of anti-dsDNA monoclonal antibody, HB2, which reacts specifically with Z-DNA and B-DNA was also tested for comparison using the same assays. The results of Table I show that the incorporation in the presence of the HB2 was similar to that obtained in the presence of the control antibodies BN18 and P3, and in the complete absence of antibody (-Ab) from the reaction mixture.

TABLE 1

Comparison on the effect of various antibody treatments on the incorporation[a] of [α−$^{32}$P]dCTP into acid precitable material in permeabilized[b] CV-1 cells.

| Time in S phase (h)[c] | mAb 2D3 | P3 | HB2[d] | BN18 | −Ab |
|---|---|---|---|---|---|
| 0 | 21.8 (3.9)[e] | 5.6 | 3.6 | 4.7 | 4.1 |
| 2 | 17.6 (3.1) | 5.6 | 4.8 | 8.4 | 6.5 |
| 4 | 18.1 (2.3) | 7.8 | 6.1 | 8.4 | 5.9 |

[a]Incorporation is expressed as $^{32}$p:$^3$H ratio (see text for explanation).
[b]The cells were synchronized in $G_1/S$ by treatment with aphidicolin, then released into S phase by removal of the drug. Treatment with the mAb, permeabilization and DNA replication are described in Materials and Methods.
[c]Time past removal of aphidicolin.
[d]Monoclonal antibody with reactivity against Z-DNA and B-DNA.
[e]Numbers in brackets indicate (−)-fold enhancement of incorporation in the presence of anti-cruciform mAb, 2D3, relative to its control antibody, P3.

In five out of eight experiments, a biphasic incorporation profile was obtained, with the two peaks occurring at 1-2 and 5-6 hours, respectively, into the S phase as shown in FIGS. 3 and 5. In the other three experiments a single peak was observed at either 3 or 4 hours. These results may reflect a temporal activation for early- and mid-S replicating clusters of replicons and the observed variations in time may be due to variations in the cell synchrony from experiment to experiment.

D. Detection of 2D3 and 4B4 Monoclonal Antibodies in the Nuclei of Permeabilized Cells In order to confirm that entry of monoclonal antibodies into the cell nucleus was achieved, samples of cells that were permeabilized and treated with 2D3 and P3 as described above were allowed to react with fluorescein-conjugated goat anti-mouse IgG in the following manner.

Permeabilized cells from log-phase cultures of CV-1, exposed to 2D3 and P3 antibody as described above, were washed twice with cold PBS containing 1% FCS. The cells were then exposed to 1 mg RNase in 0.5 ml wash medium for 30 minutes at room temperature before a third and final wash. A 0.1 ml volume of a 1/10 dilution of fluorescein-conjugated F(ab')$_2$ fragment of goat anti-murine IgG (Cappel Labortories, Cochranville, PA. USA) was added to the pellet. After 30 minutes at 4° C. it was washed three times and the pellet resuspended in 0.1 ml PBS and 1% FCS. (It should be noted that after permeabilization using NP-40 the cellular preparation consists mainly of nuclei with large amounts of attached cytoplasm. In the process of the extensive washing required to prepare the cells for immunofluorescence the adherent cytoplasm is removed leaving only the nuclei). The nuclei were placed on microscope slides and viewed with a Leitz Orthoplan fluorescence microscope.

With this indirect immunofluorescence method, 2D3 was detectable in the reacted nuclei while P3 was not.

E. Sizing of the in Vitro Replicated DNA

The DNA that was synthesized in permeabilized cells in the presence or absence of 2D3 mAb was extracted and concentrated by ethanol precipitation. Samples ($2 \times 10^5$ c.p.m.) were resuspended in 5 μl of denaturing dye mix (80% v/v formamide, 10 mM NaOH, 1 mM EDTA, 0.1% w/v xylene cyanol, 0.1% w/v bromophenol blue (Maxam and Gilbert, (1980) Methods Enzymol. 65, 499-525), denatured by boiling for 10 minutes and quick-chilled in ice. They were then loaded and electrophoresed onto a 4% polyacrylamide sequencing gel (Maxam and Gilbert, (1980) Methods Enzymol. 65, 499-525). End-labeled λ HindIII DNA was treated in the same way and was co-electrophoresed as size markers.

E. Dot-blot Hybridization Analysis of DNA Synthesized in the Permeabilized Cells In order to explain the apparent enhancement of [α-$^{32}$P]dCTP incorporation into DNA in the presence of 2D3 antibody by comparison to the control antibody, P3, we isolated the in vitro synthesized DNA from the two monoclonal antibody treatments and dot-blotted for hybridization analysis with probes, whose copy number in the monkey genome is known and whose synthesis is known to take place in the early part of S phase.

DNA was synthesized in permeabilized cells in the presence of 2D3 or P3 monoclonal antibody as described above except that, instead of [α-$^{32}$P]dCTP, cold dCTP was used at a final concentration of 0.1 mM. The isolated DNA was dot-blotted onto Genescreen Plus membranes (NEN) at concentrations of 0.25, 0.5 and 1 μg per dot, in duplicate. Dot-blotting, prehybridization and hybridization conditions were as described in Kaufmann et al., (1985) Mol. Cell Biol. 5, 721-727. The inserts of pBR/ors 8 (Zannis-Hadjopoulos et al., (1985) J. Mol. Cell. Biol. 5, 1621-1629), pSV2/DHFR (Chang et al., (1978) Nature 275, 617-624), pHSR-1 (c-myc; ATCC), pc-fos(human)-1 (C-fos; ATCC), Blur 8 (human Alu. ATCC) (Rubin et al., (1980) Nature 284, 373-374), and pCa1004, a clone of α-satellite DNA, were nick-translated to high specific activity (Rigby et al., (1977) J. Mol. Biol. 113, 237-251) and used as hybridization probes.

The amount of hybridizable radioactivity of each probe was quantitated for each time point by densitometry, as a measure of relative copy number in that particular DNA, present after each monoclonal antibody treatment. The results of Table II show that when a low-copy probe (ors 8; five copies per haploid CV-1 genome) is used, a 3- to 6-fold increase in its copy number in the DNA that was synthesized in vitro, at 1-6 hours into the S phase in the presence of 2D3 (average magnitude of [α-$^{32}$P]dCTP incorporation enhancement, 2-fold) is observed over that synthesized in the presence of P3.

TABLE II

Relative enhancement of DNA synthesis by 2D3 monoclonal antibody in permeabilized cells[a] determined by specific probes.

| Probe | Time in S Phase (h)[b] | | |
|---|---|---|---|
| | 1 | 5 | 6 |
| ors 8 | 3.1[c] | — | 5.5 |
| DHFR | 2.1 | 4.2 | — |
| c-myc | 11.2 | 3.2 | — |
| c-fos | 0.8 | 1.0 | — |

[a]Incorporation is expressed as $^{32}$p:$^3$H ratio (see text for explanation).
[b]Time past removal of aphidicolin.
[c]The relative enhancement is shown as a ratio of radioactive probe hybridized to DNA isolated from 2D3-treated cells to that isolated from P3-treated (control) cells. Radioactivity was quantitated by densitometry scanning of the dots.

Ors 8 is a 483 bp long clone of CV-1 DNA, obtained by a procedure that enriches for sequences that contain origins of replication and it can initiate autonomous replication in monkey and human cells as shown in Frappier and Zannis-Hadjopoulos, (1987) Proc. Natl. Acad. Sci. USA 84, 6668-6672). It contains an imperfect 27 bp inverted repeat at its center. Similar results were obtained using a cDNA clone of the single-copy mouse DHFR gene as probe, but this time a 2-to 5- fold amplification of copy number was observed in the DNA that was synthesized in vitro at 1-5 hours into the S phase, in the presence of 2D3; the magnitude of this enhancement was also similar to that observed for incorporation as it can be seen in FIGS. 3 and 4. Replication of mammalian DNA sequences containing the DHFR gene occurs immediately on entry of the cells into the S phase but has also been reported to occur throughout the first 5 hours of S (Heintz and Hamlin, (1982) Proc. Natl. Acad. Sci. USA 79, 4083-4087. Similarly, the in vitro synthesized DNA was probed with c-myc and c-fos, two cellular proto-oncogenes that are thought to play a role in the regulation of cell proliferation. An enhancement of 11-fold or higher, much greater than that observed for ors 8 and DHFR, was observed for c-myc in the presence of 2D3 and during the first hour of synthesis; however, the synthesis of c-fos in the presence of either 2D3 or P3 was quantitatively the same.

We claim:

1. A monoclonal antibody of class IgG produced by a hybridoma formed by fusion of cells from a mouse myeloma line and spleen cells from a mouse previously immunized with a stable heteroduplex constructed from two DNA plasmids said heteroduplex possessing at least one cruciform structure, wherein the antibody:
a) binds specifically to stable cruciform DNA structures;
b) binds specifically to heteroduplex T-shaped DNA structures;
c) does not bind to either double stranded or single stranded linear DNA;
d) does not bind to single stranded DNA containing a single stem-loop or hairpin; and
e) does not bind to native yeast tRNA.

2. The monoclonal antibody of claim 1, which is of subclass IgG1.

3. A monoclonal antibody of class IgM produced by a hybridoma formed by fusion of cells from a mouse myeloma line and spleen cells from a mouse previously immunized with a stable heteroduplex constructed from two DNA plasmids and heteroduplex possessing at least one cruciform structure, wherein the antibody:
a) binds specifically to cruciform DNA structures;
b) does not bind to heteroduplex T-shaped DNA structures;
c) does not bind to either double stranded or single stranded linear DNA;
d) does not bind to single stranded DNA containing a single stem-loop or hairpin; and
e) does not bind to native yeast tRNA 4. A monoclonal antibody of class IgG produced by a hybridoma formed by fusion of cells from a mouse myeloma line and spleen cells from a mouse previously immunized with a stable heteroduplex constructed from two DNA plasmids, said heteroduplex possessing at least one cruciform structure, wherein the antibody binds specifically to stable cruciform DNA structures synthesized as heteroduplexes in vitro, and it does not bind to either stranded or single stranded linear DNA and it does not bind to single stranded DNA containing a single stem-loop or hairpin.

5. The monoclonal antibody of claim 4, which is of class IgG1.

6. A monoclonal antibody of class IgM produced by a hybridoma formed by fusion of cells from a mouse myeloma line and spleen cells from a mouse previously immunized with a stable heteroduplex constructed from two DNA plasmids, said heteroduplex possessing at least one cruciform structure, wherein the antibody binds specifically to stable cruciform DNA structures synthesized as heteroduplexes in vitro, and it does not bind to either stranded or single stranded linear DNA and it does not bind to single stranded DNA containing a single stem-loop or hairpin.

7. The monoclonal antibody of claims 1, 2 or 3, wherein said antibody is produced from a hybridoma formed by fusion of P3-X63Ag8 myeloma cells and spleen cells from a BALB/C mouse previously immunized with heteroduplex cruciform DNA constructed from Hind III/SphI fragments of pRGM 21 and pRGM 29.

8. The monoclonal antibody of claims 4, 5 or 6, wherein said antibody is produced from a hybridoma formed by fusion of P3-X63Ag8 myeloma cells and spleen cells from a BALB/C mouse previously immunized with heteroduplex cruciform DNA constructed from Hind III/SphI fragments of pRGM 21 and pRGM 29.

9. A hybridoma having all of the identifying characteristics of ATCC HB 9328.

10. A hybridoma having all of the indentifying characteristics of ATCC HB 9329.

11. A monoclonal antibody produced by the hybridoma of claim 9.

12. A monoclonal antibody produced by the hybridoma of claim 10.

* * * * *